United States Patent [19]

Saita et al.

[11] Patent Number: 4,957,763

[45] Date of Patent: Sep. 18, 1990

[54] COMPOSITE SWEETENING AGENT

[75] Inventors: Taketsugu Saita; Junko Shindo, both of Tokyo, Japan

[73] Assignee: Kabushiki Kaisha Yakult Honsha, Tokyo, Japan

[21] Appl. No.: 356,697

[22] Filed: May 25, 1989

[30] Foreign Application Priority Data

May 30, 1988 [JP] Japan ................... 63-130161

[51] Int. Cl.$^5$ ............................................. A23L 1/236
[52] U.S. Cl. .................................................. 426/548
[58] Field of Search ........................................ 426/548

[56] References Cited

FOREIGN PATENT DOCUMENTS 63-196239  8/1988  Japan .

OTHER PUBLICATIONS

STN Data Base, File CA, CA 110(15):133962b, Abstracting JP 63/196240, (Aug. 15, 1988).
STN Data Base, File CA, CA 110(15):133961a, Abstracting JP 63/196239, (Aug. 15, 1988).
STN Data Base, File CA, CA 106(13):101092u, Abstracting JP 61/289856, (Dec. 19, 1986).
*Food Chemical*, No. 6, 1987, pp. 87–94.

*Primary Examiner*—Joseph Golian
*Attorney, Agent, or Firm*—Oblon, Spivak, McClelland, Maier & Neustadt

[57] ABSTRACT

A composite sweetening agent contains Aspartame and a galactooligosaccharide expressed by the formula: Gal-(Gal)$_n$-Glc (wherein Gal denotes a galactose residue, Glc denotes a glucose residue and n denotes an integer from 1 to 4) in a ratio by weight of 1:17 to 1:200, without having either a bitter or astringent taste.

2 Claims, No Drawings

COMPOSITE SWEETENING AGENT

BACKGROUND OF THE INVENTION

The present invention relates to a composite sweetening agent which imparts an improved quality of sweetness to Aspartame (α-L-aspartyl-L-phenyl alanine lower-alkyl ester) which is a sweetening agent.

Aspartame has a high degree of sweetness which is about 100 to 200 times that of sucrose and is very excellent with respect to its quality of sweetness when compared with synthetic high-sweetness substances used now. Aspartame also has substantially no caloric value and is frequently used as a diet sweetening agent. Aspartame, however, has disadvantages with respect to its feeling of bitter and astringent taste and its unsatisfactory richness.

A conventional means for resolving the above-described disadvantages of Aspartame is a means in which Aspartame is mixed with another sweetening substance to form a composite sweetening agent, whereby good results are obtained to some extent. For example, the method disclosed in Japanese Patent Laid-Open No. 149358/1985 is a method in which the disadvantages with respect to the quality of sweetness of Aspartame are removed by mixing fructooligosaccharide with Aspartame. The fructooligosaccharide used in this method, however, has a high degree of sweetness which is about 30 to 40% of that of sucrose. It might be considered that the fructooligosaccharide contains a high ratio of monosaccharides such as glucose and fructose and the like which have good sweetness and which are produced depending upon the production method used. It is therefore apparent that such monosaccharides function as necessary constituent components of a sweetening agent and it is recognized that fructooligosaccharide itself does not improve the quality of sweetness of Aspartame.

It is an object of the present invention to provide a novel means for resolving the above-described disadvantages of Aspartame without losing any of the characteristics thereof.

SUMMARY OF THE INVENTION

The present invention provides a composite sweetening agent characterized by containing Aspartame and galactooligosaccharide expressed by the formula: Gal-(Gal)$_n$-Glc (wherein Gal denotes a galactose residue, Glc denotes a glucose residue and n denotes our integer from 1 to 4) in a ratio by weight of 1:17 to 1:200.

DETAILED DESCRIPTION OF THE INVENTION

It is already known that galactooligosaccharide as used in the present invention is useful as a growth-promoting substance for bifidobacteria which are useful bacteria living in human intestines and which are principal constituent components of breast milk oligosaccharide. Thus galactooligosaccharide has been recently employed in various fields, for example, it has been added to fermented milk or dried milk used for childcare. There have been no examples which use galactooligosaccharide as a sweetening agent in spite of its advantage in terms of resistance to digestion and a low caloric value because the degree of sweetness thereof is only about 20% of that of sucrose.

Galactooligosaccharide can be produced by a method in which lactose is reacted with β-galactosidase derived from *Aspergillus oryzae* (refer to Japanese Patent Laid-Open No. 20266/1983) or a method which utilizes *Cryptococcus* (refer to Japanese Patent Laid Open No. 251896/1985). Such a method generally produces a sugar mixture containing about 30 to 70% of galactooligosaccharide, disaccharides mainly comprising unreacted lactose and monosaccharides such as glucose, galactose and so on which are secondary products. Such a sugar mixture may be used as it is as the sweetening agent of the present invention. Although the lactose and monosaccharides contained in the mixture have no adverse effect on the quality of the sweetness, however, when it is preferable that such saccharides do not serve as caloric sources, it is preferable to reduce the amount of the lactose remaining unreacted or to decompose or remove the monosaccharides by any desired method.

Galactooligosaccharide may be mixed with Aspartame in a liquid state or a powdery state. As already known, Aspartame is unstable in a neutral aqueous solution and is thus preferably dried to form a powder after being mixed with the galactooligosaccharide in a solution state. When the thus-formed mixture is stored in the form of an aqueous solution, it must be maintained in a weak acid state at a pH value of 6 or less.

The mixing ratio of Aspartame and the galactooligosaccharide is that described above. A particularly preferable mixing ratio is 25 to 50 parts of galactooligosaccharide to 1 part of Aspartame. An amount of galactooligosaccharide greater than the above-described value causes an inCrease in the amount that is necessary to obtain the necessary degree of sweetness and is thus undesirable for use, and it also causes an increase in the concentration thereof in sweetened food and drink and thus a deterioration in the taste of the products, depending upon the conditions used. If the amount of the galactooligosaccharide mixed is insufficient, the disadvantages of Aspartame remain unresolved (refer to the Experimental Example described later).

If the galactooligosaccharide is accompanied with glucose and or galactose, which are the secondary products in the production process thereof, there is no adverse effect on the quality of sweetness of the sweetening agent of the present invention because the monosaccharides themselves have a good quality of sweetness, as is already known. In order to prevent any significant deterioration in Aspartame's quality of having substantially no caloric value, however, the amount of monosaccharides contained in the sweetening agent of the present invention is preferably less than about 30% by weight.

EXPERIMENTAL EXAMPLE

The qualities of sweetness of each of the aqueous solutions containing the purified galactooligosaccharide produced in Example I and Aspartame and a mixture thereof were sense tested by 12 trained panel members. The tests were performed using the absolute 5 ranks described below. Each of the samples was so prepared as to have a degree of sweetness that is equivalent to that of an aqueous solution of 8% sucrose.

2 marks: Good
1 mark: Somewhat good
0 mark: Medium
−1 mark: Somewhat poor
−2 marks: Poor The results obtained are shown in Table 1. The average of the scores of the 8% aqueous sucrose solution, used as a control, was 0.41. It is recognized that the values decrease within a range of high ratios of the galactooligosaccharide mixed owing to the effect of an increase in the concentration of solids which was caused by preparing each sample so as to have a degree of sweetness equivalent to that of the 8% sucrose solution.

TABLE 1

| Mixing ratio (by weight) | | Average score |
|---|---|---|
| Galactooligo-saccharide | Aspartame | |
| 100 | 0 | −0.20 |
| 100 | 0.1 | −1.0 |
| 100 | 0.5 | 0.13 |
| 100 | 1.0 | 0.19 |
| 100 | 2.0 | 0.25 |
| 100 | 3.0 | 0.38 |
| 100 | 4.0 | 0.27 |
| 100 | 5.0 | 0.13 |
| 100 | 6.0 | 0.05 |
| 100 | 7.0 | −0.16 |
| 100 | 8.0 | −0.48 |
| 0 | 100 | −0.65 |

EXAMPLE 1

4 kg of food grade lactose was dissolved in 2.4 l of hot water, and 80000 units of β-galactosidase derived from *Aspergillus oryzae* was added to the thus formed solution, followed by reaction for 2 hours at 67° C. The reaction solution was then heated at 95° C. for 10 minutes to that the enzyme was deactivated. After the reaction solution had been diluted to 50% of a solid concentration, 5000 units of β-galactosidase prepared from *Streptococcus thermophilus* were added to the diluted solution, which was then reacted at 45° C. for 40 hours. The reaction solution was then heated at 90° C. for 10 minutes so that the enzyme was deactivated, and was then filtered by using carbon powder and Celite, which were added thereto, to form a colorless and transparent sugar solution.

A concentrated solution of the thus-formed sugar solution (galactooligosaccharide 27.8%, disaccharides 21.1%, monosaccharide 26.1% and water 25%) was purified by chromatography using a cation exchange resin to obtain a purified sugar solution with a sugar concentration (Bx) of 75 (galactooligosaccharide content, 64%; solids content: galactooligosaccharide 85% and lactose 15%). 500 parts by weight of an aqueous solution of Aspartame (concentration, 1.92%) was mixed with 500 parts by weight of the purified sugar solution obtained to form a composite sweetening agent having the form of syrup. The astringent taste, bitter taste and bad aftertaste which are peculiar to Aspartame were removed from the sweetening agent formed. The sweetening agent thus had a satisfactory quality of sweetness similar to that of sucrose. The degree of sweetness of the sweetening agent was about 160, assigning a degree of sweetness to sucrose of 100. Comparison with sucrose having the same degree of sweetness showed that the caloric value of the sweetening agent was 3% that of sucrose.

The powder product obtained by spray-drying the syrup formed has a good quality of sweetness, comparable to that of the syrup.

EXAMPLE 2

200 parts by weight of an aqueous solution of Aspartame (concentration, 2.04%) was added to 800 parts by weight of the sugar solution produced in Example 1 (not concentrated, galactooligosaccharide 17%, monosaccharides 15%) and then mixed therewith to obtain a syrup-like composite sweetening agent. The astringent taste, bitter taste and bad aftertaste peculiar to Aspartame were removed from the syrup formed. The sweetening agent thus had a satisfactory quality of sweetness similar to that of sucrose. The degree of sweetness of the sweetening agent was about 86, assigning a degree of sweetness to sucrose of 100. Comparison with sucrose having the same degree of sweetness showed that the caloric value of the sweetening agent was 37% of that of sucrose.

The powder product obtained by spray-drying the syrup formed had good quality of sweetness in the same manner as with the syrup.

EFFECT OF THE INVENTION

As described above, the composite sweetening agent of the present invention exhibits none of the disadvantages peculiar to Aspartame with respect to its quality of sweetness, and has a good quality of sweetness similar to that of sucrose. Since galactooligosaccharide has resistance to digestion, the addition thereof to Aspartame causes only a small increase in the caloric value. The present invention also has advantages in that a large amount of galactooligosaccharide contained in the sweetening agent is a growth-promoting substance for bifidobacteria and thus there are no concerns about safety and in that a healthy effect can be thus expected.

The sweetening agent of the present invention is therefore useful as a low-calorie sweetening agent which can be used in various fields.

What is claimed is:

1. A composite sweetening agent comprising: Aspartame and a galactooligosaccharide expressed by the formula: Gal-(Gal)$_n$-Glc wherein Gal denotes a galactose residue, Glc denotes a glucose residue and n denotes an integer from 1 to 4, in a ratio by weight of 1:17 to 1:200.

2. A composite sweetening agent according to claim 1 which further comprises glucose and/or galactose.

* * * * *